United States Patent [19]

Curran

[11] 3,981,878
[45] Sept. 21, 1976

[54] 4-PHENYLMERCAPTOPIPERIDINE NITRILES

[75] Inventor: Adrian Charles Ward Curran, Reading, England

[73] Assignee: John Wyeth & Brother Limited, Maidenhead, England

[22] Filed: May 10, 1974

[21] Appl. No.: 468,726

Related U.S. Application Data

[63] Continuation-in-part of Ser. No. 299,995, Oct. 24, 1972, Pat. No. 3,845,064.

[30] Foreign Application Priority Data

Oct. 29, 1971 United Kingdom............... 50431/71

[52] U.S. Cl............................ 260/293.73; 424/263; 424/267; 260/294.9
[51] Int. Cl.² ....................................... C07D 211/60
[58] Field of Search............ 260/294.9, 293.73, 299, 260/995

[56] References Cited
FOREIGN PATENTS OR APPLICATIONS 900,448   7/1962   United Kingdom.............. 260/294.9

OTHER PUBLICATIONS

Schenker et al. (I), "Helv. Chim. Acta" vol. 42, (1959), 2571–2576.

Lyle et al., "Chem. Abstracts" vol. 73, (1970), No. 55290g.
Schenker et al. (II), "Chem. Abstracts" vol. 54, (1960), 9912e.

Primary Examiner—Natalie Trousof
Assistant Examiner—R. W. Ramsuer

[57]           ABSTRACT

The invention provides a compound of formula I

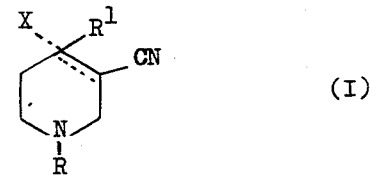

wherein the dotted lines in the ring indicate an optional double bond, X, which is present only when the ring is saturated, is S-Phenyl, R is selected from loweralkyl and phenylloweralkyl and $R^1$ is selected from hydrogen and loweralkyl and when X is absent $R^1$ is loweralkyl and the acid addition salts thereof. The new compounds provided are useful as anti-ulcer pharmaceuticals.

2 Claims, No Drawings

4-PHENYLMERCAPTOPIPERIDINE NITRILES

The invention relates to novel heterocyclic compounds and is a continuation-in-part of my copending application Ser. No. 299,995 filed Oct. 24, 1972, now U.S. Pat. No. 3,845,064, issued Oct. 29, 1974.

The invention provides a compound of formula I

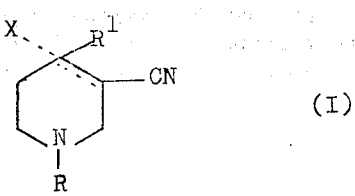

(I)

wherein the dotted lines in the ring indicate an optional double bond, X, which is present only when the ring is saturated, is S-Phenyl, R is selected from loweralkyl and phenylloweralkyl and $R^1$ is selected from hydrogen and loweralkyl and when X is absent $R^1$ is loweralkyl and the acid addition salts thereof.

When either of R and $R^1$ is a lower alkyl radical it may be a straight or branched chain, having from 1 to 6 carbon atoms, e.g. methyl, ethyl, propyl or butyl but preferably has from 1 to 3 carbon atoms. When R is a phenyl-loweralkyl group the lower alkyl portion may be as discussed above for a lower alkyl group. The alkyl groups may be substituted e.g. by a halogen atom or an alkoxy group.

The preferred phenyl groups for the phenyl portion of phenyl-alkyl group R may be substituted for example by a halogen atom, or an alkyl, alkoxy, nitro or haloalkyl (e.g. trifluoromethyl) radical.

The compounds of formula (I) can form acid addition salts with inorganic acids e.g. hydrochloric, hydrobromic, sulphuric and nitric acid or organic acids e.g. oxalic, fumaric, maleic and tartaric acid.

The compounds of formula I may be used in pharmaceutical compositions with a pharmaceutical carrier.

For the pharmaceutical carrier any suitable carrier known in the art can be used to prepare the pharmaceutical compositions. In such a composition, the carrier may be a solid, liquid or mixture of a solid and liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in suitable organic solvent, for instance aqueous propylene glycol or polyethylene glycol solutions. Aqueous propylene glycol containing from 10 to 75% of the glycol by weight is generally suitable. In other instances compositions can be made by dispersing the finely divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

Compounds of formula I have been shown to possess pharmacological activity, namely, anti-ulcer activity. The anti-ulcer activity was determined by the method of Brodie and Hanson, Gastroenterology 38, 353, 1960. 1-Benzyl-1,2,5,6-tetrahydro-4-methyl nicotinonitrile showed good activity in this test.

The anit-ulcer composition of the invention will be administered orally in either liquid or solid composition form. These compositions may include one or more antacid ingredients, e.g. aluminium hydroxide, magnesium hydroxide or bismuth carbonate, aluminum glycinate, calcium carbonate, magnesium trisilicate, sodium bicarbonate or the alumina gel described in British patent specification No. 1,284,394.

The compounds of formula I are also useful as intermediates for the preparation of compounds of formula II

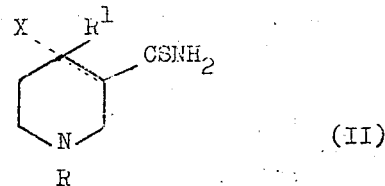

(II)

wherein X, R and $R^1$ are as defined in connection with formula I and the dotted line has the same significance as in formula I. Compounds of formula II are described in copending application Ser. No. 299,995 (now U.S. Pat. No. 3,845,064, granted Oct. 29, 1974) as is their preparation from compounds of formula I. Thus a compound of formula I wherein X is S-Ph may be treated with $H_2S$ to give the corresponding compound of formula II. A compound of formula I wherein X is absent and R and $R^1$ are as defined above may be treated with a thioamide of formula

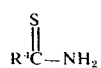

where $R^4$ is an alkyl group of 1–6 carbon atoms preferably a methyl group in dimethyl formamide saturated with hydrogen chloride to give the corresponding compound of formula II wherein R and $R^1$ are as defined above.

The nitriles of formula I wherein X is SPh may be prepared by treatment of a nitrile of formula IV

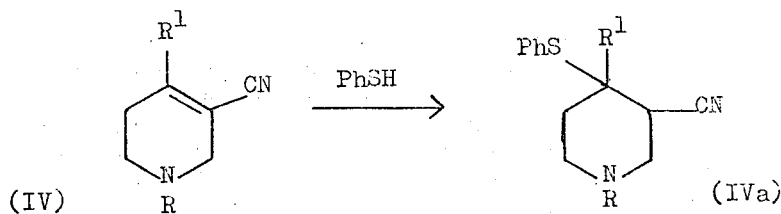

with thiophenol to give a compound of formula IVa.

The nitriles of formula I wherein X is absent may be prepared by reduction of a corresponding 3-cyanopyridine of formula (XI) wherein R and $R^1$ are as defined in connection with formula (I), and Z is an anion e.g. a halide ion.

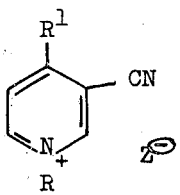

The reduction is conveniently carried out with a boro-hydride e.g. an alkali-metal borohydride especially sodium borohydride.

Another method of preparing nitriles of formula I comprises cyclising an open chain compound in the presence of a basic condensing agent. Any strong base will suffice such as an alkali metal alkoxide e.g. sodium methoxide or ethoxide, sodium amide or Triton B (benzyltrimethyl ammonium hydroxide). Thus a compound of formula (XII) wherein R and $R^1$ are as defined in connection with formula I

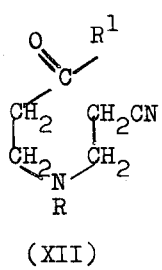

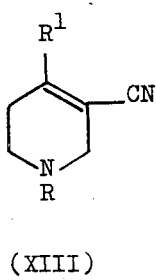

can be cyclised to a compound of formula (XIII). The reaction can be carried out in a suitable inert solvent e.g. benzene and the water removed by azeotropic distillation. Sometimes an intermediate compound of formula (XIV)

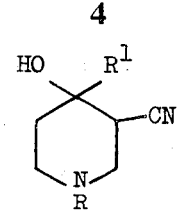

wherein R and $R^1$ are as defined in connection with formula (XII) is formed as a byproduct. This compound can be separated usually by fractional crystallisation but can be further dehydrated by heating to a compound of formula (XIII) if desired. Often distillation of the crude product of the cyclisation reaction will suffice to effect dehydration of XIV.

A nitrile in which R is alkyl or aralkyl may be prepared by alkylation of a corresponding compound where R is hydrogen using standard alkylating conditions. Thus a compound of formula (XV) wherein $R^1$ is as defined in connection with formula I can be alkylated

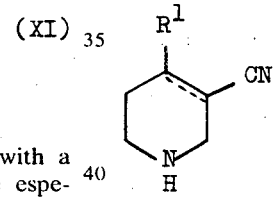

to give a compound of formula (XVI) wherein R is alkyl or aralkyl. The starting compound of formula (XV) when the double bond is absent can be prepared by hydrogenation of the corresponding N-benzyl compound. Alternatively compound (XV) can be obtained from compound (XII) as defined above, where R is hydrogen.

Methods of preparing the novel nitriles of the invention are also included in the invention.

The following examples illustrate the invention:

EXAMPLE 1

A. 3-Cyano-1-methyl-1,2,5,6-tetrahydropyridine hydrochloride

The title compound was prepared from 1-methyl-3-cyanopyridium iodide by reduction with sodium borohydride, according to Helv. Chim. Acta. 1959, 42, 1969–70, and obtained in 30% yield b.p. 98°–100°C/15 mm.Mg. The hydrochloride was prepared by dissolving the free base (1 g.) in dry ether (50 ml.) and treating with dry hydrogen chloride gas for 5 minutes with cooling. The solid was filtered and recrystallised from ethanoldiethylether as colourless needles m.p. 227°C.

Found: C, 53.10; H, 6.90; N, 17.7. $C_7H_{10}N_2HCl$ requires: C, 53.04; H, 7.01; N, 17.70%.

B. 1-Methyl-4-phenylmercaptonipecotonitrile

A mixture of 3-cyano-1-methyl-1,2,5,6-tetrahydropyridine (6.1 g 0.05 m.) thiophenol (5.50 g., 0.05 m.) and pyridine (1 ml.) was stirred at room temperature for 1 hour, diluted with dioxan (7 ml.) and heated at 110° with stirring for 24 hours. The solvent was removed in vacuo and the residual brown oil diluted with benzene (100 ml.) washed with N/1 hydrochloric acid (3 × 25 ml.) and the combined washings made basic, with 2N sodium hydroxide and extracted into benzene (3 × 25 ml). The combined extracts were washed with saturated brine, dried ($MgSO_4$) and evaporated to give a residual solid. Recrystallisation from benzene − 60°/80° petroleum ether gave the title compound as colourless plates (8 g., 75%) m.p. 114°C. Found: C, 67.42; H, 6.97; N, 11.99. $C_{13}H_{16}N_2S$ requires: C, 67.21; H, 6.94; N, 12.06%.

1-Methyl-4-phenylmercaptonipectonitrile displays anti-ulcer activity.

EXAMPLE 2

1-Benzyl-1,2,5,6-tetrahydro-4-methylnicotinontrile

A mixture of β-cyanoethylbenzylamine (92g.), conc hydrochloric acid (60 ml.), ethanol (120 ml.), paraformaldehyde (30 g.) and acetone (120 ml.) were heated at reflux for 5 hours. The solvent was removed in vacuo and the residue dissolved in water (100 ml.) and washed with ether (2 × 100 ml.). The aqueous solution was made basic with aqueous potassium carbonate and the solution extracted with ether (3 × 100 ml.). The combined extracts were dried and evaporated to give N-benzyl-N-(2-cyanoethyl)-4-aminobutan-2-one (132 g) which was dissolved in dry benzene (1.3 liter) and sodium methoxide (prepared from sodium (13.2g) was added portionwise. The mixture was refluxed for 5 hours and the cooled solution washed with 2N HCl (4 × 500 ml.). The combined extracts were made basic with potassium carbonate and extracted into methylene chloride (4 × 500 ml.) and the combined extracts dried ($MgSO_4$) and solvent removed in vacuo. The residual oil was distilled to give 1-benzyl-3-cyano-4-methyl-1,2,5,6-tetrahydropyridine as a colourless oil (40 g.) b.p. 136°C/5 × $10^{-3}$ mm. Hg. which was converted to the hydrochloride by treating an ethereal solution with dry HCl gas. The resultant solid was recrystallised from methanol-ether giving the hydrochloride of the title compound as colourless needles (35 g.) m.p. 172°C. Found: C, 68.0; H, 7.0; N, 11.3% $C_{14}H_{16}N_2HCl$ requires C, 67.6; H, 6.9; N, 11.3%.

I claim:

1. A compound of the formula

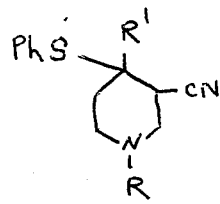

wherein R is loweralkyl or phenylloweralkyl, $R^1$ is hydrogen or loweralkyl and Ph is phenyl, or a pharmaceutically acceptable acid addition salt thereof.

2. A compound as claimed in claim 1, which is 1-methyl-4-phenyl mercaptonipectonitrile.

* * * * *